United States Patent [19]

Sbragia et al.

[11] 4,224,338

[45] Sep. 23, 1980

[54] SIMULTANEOUS FUNGICIDAL AND MITICIDAL PROTECTION OF PLANTS EMPLOYING CERTAIN TIN COMPOUNDS

[75] Inventors: Ronald J. Sbragia, Clayton, Calif.; John L. Hardy, Fork Union, Va.; John E. Engelhart, Westfield; Melvin H. Gitlitz, Edison, both of N.J.; Robert J. Ehr, Pittsburg, Calif.

[73] Assignees: The Dow Chemical Company, Midland, Mich.; M&T Chemicals Inc., Rahway, N.J.

[21] Appl. No.: 715,072

[22] Filed: Aug. 17, 1976

[51] Int. Cl.$^2$ .................... A01N 9/00; A01N 9/36; C07F 7/22
[52] U.S. Cl. .................... 424/288; 260/429.7; 424/225
[58] Field of Search .................... 424/288, 225; 260/429.7

[56] References Cited

U.S. PATENT DOCUMENTS

| 3,400,201 | 9/1968 | Mocotte | 424/288 |
| 3,892,862 | 7/1975 | Gitlitz | 424/288 |
| 3,892,863 | 7/1975 | Gitlitz et al. | 424/288 |

FOREIGN PATENT DOCUMENTS 1059629  2/1967  United Kingdom.

*Primary Examiner*—Helen M. S. Sneed
*Attorney, Agent, or Firm*—Edward E. Schilling

[57] ABSTRACT

Method of protecting plants from both fungal organisms and mites in the same treatment in which there is applied to the plant an amount of one or more of selected tricyclopentyl tin and tris(cyclopentylmethyl)tin compounds, which amount is sufficient to provide both antifungal and miticidal protection but is less than a substantially harmful phytotoxic amount. Counter ions in these compounds which are suitable include hydroxy, halo, oxo, thioxo, alkyl- and aryl carboxylate, thiocyanato, diloweralkyldithiocarbamoyl and diethoxyphosphinothioylthio.

34 Claims, No Drawings

SIMULTANEOUS FUNGICIDAL AND MITICIDAL PROTECTION OF PLANTS EMPLOYING CERTAIN TIN COMPOUNDS

BACKGROUND OF THE INVENTION

1. Field of the Invention

The invention relates to a method of protecting plants against both plant pathogenic fungal organisms and mites on applying a single type of chemical effective against both the fungi and the mites.

2. Description of the Prior Art

Chemical agents which are effective against both plant pathogenic fungal organisms and mites at the same application dose rate are believed to be rare. Tricyclohexyl tin compounds such as those described in U.S. Pat. No. 3,264,177 are effective miticides but have very low if any fungicidal activity at miticidal dosage rates. Bis-(triorganotin) sulfates and sulfites, including such tricycloalkyl tin compounds as tricyclopentyl tins, tricyclohexyl tins and tricyclooctyl tin compounds are described broadly in U.S. Pat. No. 3,391,174 as having antifungal, bacteriostatic, nematocidal, miticidal and insecticidal activities. Other tricyclopentyl tin compounds have been prepared and described as having antifungal activity, but so far as is known there has been no suggestion that such compounds also have miticidal activity when applied to plants at effective antifungal dose rates and in less than seriously harmful phytotoxic amounts.

Some of the compounds used according to the invention described herein are old and others are new. The methodsa of preparation of the tricycloalkyl tin compounds are generally known. For example, tri(cyclopentyl) tin and tri(cyclopentylalkyl) tin halides wherein the halogen is chlorine, bromine or iodine can be prepared by reacting at least 3 moles of the corresponding cyclopentyl or cyclopentylalkyl magnesium halide with one mole of an alkyl tin trihalide. The resultant tetraorgano tin compound is reacted with an equimolar amount of a second tetravalent tin compound wherein the groups on the tin are each a group to serve as a counter ion in the desired product compound. During the reaction, one of the lower alkyl groups present on the tetraorgano tin compound is replaced by one of the groups from the second tetravalent tin compound. The reactions may be represented as follows:

3-cyclopentylMgX+RSnY₃=(cyclopentyl)₃SnR+3MgXY(cyclopentyl)₃SnR+SnZ₄=(cyclopentyl)₃SnZ+RSnZ₃ wherein X and Y each independently represent chlorine, bromine or iodine, R is lower alkyl and Z is a functional group selected from, e.g., hydroxyl, bromine, chlorine, iodine,

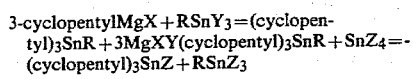

The preparation should be carried out under anhydrous conditions at from ambient to slightly elevated temperatures and in an aprotic hydrocarbon solvent. The preparation of alkyl tin trihalides is described in U.S. Pat. No. 3,340,283. The reaction conditions which may be employed will be better understood with reference to the comprehensive treatment in an article by R. K. Ingham et al. appearing in the October 1960 issue of *Chemical Reviews* at pages 459–539.

The preparation of tricycloalkyl tin halides is also described in U.S. Pat. No. 3,595,892. Other compounds than the halides may be similarly prepared.

Further reference is made to Berichte der deutschen chemischen Gesellschaft 47, 3257–66 (1914); ibid., 57B, 532–44 (1924); British Pat. No. 760,056; and French Pat. No. 1,253,725; wherein are described methods of preparing tricyclohexyl tin compounds by methods which are generally applicable to the preparation of the present tricyclopentyl tin and tricyclopentylmethyl tin compounds.

STATEMENT OF THE INVENTION

It has now been discovered that plants may be protected from plant pathogenic fungal organisms and mites in the same treatment by applying to the plants to be protected an amount of one or more compounds of the formula

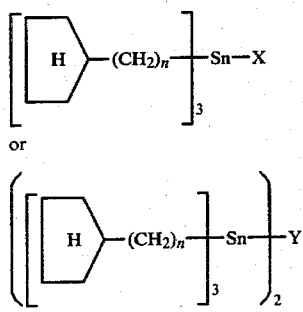

or

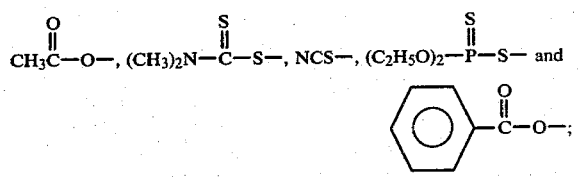

wherein

X is a member of the group consisting of hydroxyl, bromo, chloro, fluoro,

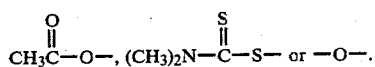

Y is a chalcogen selected from O and S; and n is 0 or 1; which said amount is at least an effective antifungal amount and likewise at least an effective miticidal amount, but less than a substantially harmful pytotoxic amount. For the purposes of the specification and claims slight phytotoxicity is slight epidermal leaf damage from which a plant recovers. Substantially harmful phytotoxicity is a noticeably more serious epidermal leaf damage effect.

The present tin compounds, preferably selected from tricyclopentyl hydroxy stannane, hexacyclopentyl distannoxane, tricyclopentyl 3-(((dimethylamino)thioxomethyl)-thio)stannane, tricyclopentyl((diethoxyphosphinothioyl)-thio)stannane, or tricyclopentyl acetyl stannane, are applied as a formulated dust admixed in an inert solid carrier, but more preferably as an aqueous dispersion containing one or more surface active materials.

DETAILED DESCRIPTION OF THE INVENTION

The tin compounds employed according to the present invention are crystalline solid materials which are somewhat soluble in many common organic solvents and most of them are of low solubility in water. When used according to the invention, these compounds are adapted readily and conveniently to be employed as toxicants in the control of plant pathogenic fungal organisms and mites which particularly attack economic plants. For the purposes of the present description and the appended claims, the term plants is meant to include cranberry bean, common garden bean, tobacco, grapes, apple trees, rice, cotton, cucumbers and wheat, or parts thereof, such as specialized leaf parts, blossoms, fruit or new growth portions.

As indicated above, these compounds may be prepared for application in the form of dust compositions or water dispersions.

In the preparation of dust compositions, the triorgano tin compound can be blended with many commonly employed finely divided solid carriers such as fullers earth, attapulgite, bentonite, pyrophyllite, vermiculite, diatomaceous earth, talc, chalk, gypsum and wood flour. The carrier, usually in a finely divided form, is ground or mixed with the toxicant or wetted with a dispersion of the toxicant in a volatile liquid. Depending upon the relative proportions of toxicant and carrier, these compositions can be employed as concentrates that are subsequently diluted with additional solid carrier to obtain the desired amount of active ingredient for field application. Alternatively, such concentrate dust compositions can be employed in combination with various known anionic, cationic or non-ionic surfactants as emulsifying or dispersing agents to form spray concentrates. Such concentrates may also be prepared by preparing the tin compound in finely divided form as by milling, and dispersing the compounds in one or more of the said surfactants in aqueous medium.

The choice and concentration of surfactant are determined by the ability of the material to facilitate the dispersing of the concentrate in the liquid carrier to produce the desired liquid composition. Suitable liquid carriers include water, methanol, ethanol, isopropanol, methyl ethyl ketone, acetone, methylene chloride, chlorobenzene, toluene, xylene and petroleum distillates. Among the preferred petroleum distillates are those boiling under 400° F. at atmospheric pressure and having a flash point above about 80° F.

Liquid compositions can also be prepared by dissolving one of the present triorgano tin compounds in a mixture containing a water-immiscible organic liquid and a surface active dispersing agent. The resulting emulsifiable concentrate is then further diluted with water and/or an oil to form spray mixtures in the form of oil and water emulsions. In such compositions, the carrier comprises an aqueous emulsion, i.e., a mixture of water-immiscible solvent, emulsifying agent and water. Preferred dispersing agents for these compositions are oil-soluble and include the condensation products of alkylene oxides with phenols and organic and inorganic acids, polyoxyethylene derivatives of sorbitan esters, alkylarylsulfonates, complex ether alcohols, mahogany soaps and the like. Suitable organic liquids to be employed in the compositions include petroleum distillates, hexanol, liquid halohydrocarbons and synthethic organic oils. The surface active dispersing agents are usually employed in the liquid dispersions and aqueous emulsions in the amount of from about 1 to about 20 percent by weight of the combined weight of the dispersing agent and the active toxicant.

When operating in accordance with the present invention, the triorgano tin compound or a composition containing the compound can be applied directly onto the organism to be controlled or to the site to be protected, particularly plants including trees and vines. Application to the foliage of plants is conveniently carried out using power dusters, boom sprayers and other power spraying equipment as well as manually operated devices. When employed in this manner, the compositions should not contain any significant amounts of phytotoxic diluents. In large scale operations, dust or low volume sprays may be applied from an aircraft.

Suitable dust concentrates, emulsion concentrates or water-dispersible concentrates may contain from about 5 to about 95 percent by weight of one or more of the present triorgano tin compounds, and more generally about 20 to about 90 percent by weight of the active toxicant.

The compositions diluted for use in normal high volume methodology will contain from about 25 to about 600 parts per million by weight of the triorgano tin compound, and more preferably about 100 to about 300 parts per million in order to achieve both antifungal and miticidal results upon applying the prepared composition to plants to be protected. In certain cases where low volume applications are desired, the concentrations set forth above will need to be increased accordingly as the volume applied per unit of area is reduced.

The triorgano tin compounds of particular interest serving as toxicants in the method of the invention, include tricyclopentyl hydroxystannane, hexacyclopentyl distannoxane, hexacyclopentyl distannathiane, tricyclopentyl chlorostannane, tricyclopentyl bromostannane, tricyclopentyl fluorostannane, tricyclopentylthiocyanato stannane, tricyclopentyl benzoylstannane, tris(cyclopentylmethyl) bromostannane, tris(cyclopentylmethyl)chlorostannane, tricyclopentyl 3-(((dimethylamino)thioxomethyl)thio) stannane, tricyclopentyl (((2-ethyl-1-oxo-hexyl)oxy) stannane, tricyclopentyl ((diethoxyphosphinothioyl)thio)stannane and tricyclopentyl acetyl stannane. Of these, the more preferred compounds are tricyclopentyl hydroxystannane, hexacyclopentyl distannoxane, tricyclopentyl chlorostannane, tricyclopentylacetylstannane, tricyclopentyl((diethoxyphosphinothioyl)thio)stannane and tricyclopentyl 3-(((dimethylamino)thioxomethyl)thio) stannane. The most preferred compounds are the tricyclopentyl hydroxystannane and the hexacyclopentyl distannoxane.

If desired, the compounds of the present invention may be applied to plants in combination with other organo tin compounds not exhibiting substantial phytotoxic effects in order to supplement or implement the activities of the present compounds. It may also be desired to apply the present compounds to plants in admixture with other toxicants such as the phosphate and thiophosphate esters which serve suitably as insecticides, or in admixture with herbicides such as the substituted triazines, the substituted ureas, the substituted propionic acids and their salts and esters, the phenoxy alkanoic acids and their salts and esters, and the like, in particular to reduce the tendency of mites to migrate from more abundant weeds to undamaged crop plant species.

The following examples are illustrative of the practice of the invention and include the best embodiments of the present invention now known.

EXAMPLE 1

A 10,000 ppm acetone concentrate of tricyclopentyl hydroxy stannane (TCPT-H) was prepared and 0.25 ml of the concentrate was added to 25 ml of 20% isopropanol in water to give a 100 ppm solution. The chemical was sprayed onto the leaf underside of a grape seedling grown in a two-inch pot. When the chemical had dried, the same leaf was inoculated with an aqueous solution of downy mildew (*Plasmopara viticola*) spores and moved to conditions conducive to the development of infection. One week later the untreated checks were uniformly infected while the treated plant showed the following result:

| Treatment | % Disease Control at 100 ppm |
|---|---|
| TCPT-H | 100 |
| Untreated check | 0 |

EXAMPLE 2

A 10,000 ppm acetone concentrate of TCPT-H was prepared and 0.25 ml of the concentrate was added to 25 ml of 20% isopropanol in water to give a 100 ppm solution. The chemical was sprayed onto apple seedling leaves that had been inoculated two days earlier with apple scab (*Venturia inaequalis*) spores and moved to conditions conducive to the development of infection. Twelve days later the untreated checks were uniformly infected while the treated plants showed the following result:

| Treatment | % Disease Control at 100 ppm |
|---|---|
| TCPT-H | 93 |
| Untreated check | 0 |

EXAMPLE 3

TCPT-H was dissolved in acetone to give a 1000 ppm concentrate from which 1 ml of the concentrate was added to 9 ml of 20% isopropanol in water, to give a 100 ppm solution. Three fourfold dilutions were prepared to give a 100, 25, 6.2 and 1.5 ppm dilution series. The diluted solutions were then applied to the foliage of grape seedlings. When the plants had dried, they were inoculated with an aqueous suspension of downy mildew (*Plasmopara viticola*) conidia and moved into conditions conducive to the development of infection. By way of a comparison test, the same procedure was repeated using, as the active ingredient, tetrachloroisophthalonitrile (TCI).

After one week the checks were uniformly infected with downy mildew while the treated plants showed the following results:

| Treatment | % Disease Control at Indicated Dosage, ppm | | | |
|---|---|---|---|---|
| | 100 | 25 | 6.2 | 1.5 |
| TCPT-H | 95* | 50 | 0 | 0 |
| TCI | 100 | 90 | 25 | 0 |

*Slight phytotoxicity

EXAMPLE 4

12 mg of each of TCPT-H and a comparison compound TCI were weighed out and formulated as 50% wettable powders. 1 ml of water was added to both TCPT-H and the TCI and for fourfold dilutions were prepared as in the previous example except that the dosages were 1200, 300, 75 and 19 ppm. After treatment, the grapes were moved into the greenhouse for four days prior to inoculation. One week later the untreated checks were uniformly infected with downy mildew while the treated plants showed the following results:

| Treatment | % Disease Control at Indicated Dosage, ppm | | | |
|---|---|---|---|---|
| | 1200 | 300 | 75 | 19 |
| TCPT-H | 99* | 95* | 25 | 0 |
| TCI | 100 | 100 | 50 | 0 |

*Slight phytotoxicity

EXAMPLE 5

A dilution series of each of TCPT-H and a comparison compound, benomyl, i.e., (methyl 1-(butylcarbamoyl)-2-benzimidazolecarbamate, was prepared as in Example 3. The diluted solutions were then sprayed onto the upper surfaces of the leaves of small apple seedlings. When the plants had dried, they were inoculated with an aqueous suspension of apple powdery mildew (*Podosphaera leucotricha*) conidia. One week later, the untreated checks were uniformly infected with mildew while the treated plants showed the following results:

| Treatment | % Disease Control at Indicated Dosage, ppm | | |
|---|---|---|---|
| | 100 | 25 | 6.2 |
| TCPT-H | 100 | 95 | 25 |
| Benomyl | 99 | 100 | 99 |

EXAMPLE 6

Five days after inoculation with mildew, apple seedlings were treated with a 100 ppm solution of TCPT-H, while other seedlings were treated with a 100 ppm solution of benomyl in a comparison run. One week after the treatments, the untreated checks were uniformly infected while the treated surfaces showed the following percent disease eradication:

| Treatment | % Disease Eradication at 100 ppm |
|---|---|
| TCPT-H | 99 |
| Benomyl | 90 |

EXAMPLE 7

From a 50% wettable powder formulation of each of TCPT-H and a comparison compound O-ethyl-S,S-diphenyl phosphorodithioate (EDPD) a 1200, 300, 75 and 19 ppm dilution series was prepared in 20% isopropanol in water. Rice seedlings about 7 inches tall were then treated and the treated rice was then moved into the greenhouse. Three days later, the rice was inoculated with rice blast and moved to conditions conducive to the developments of infection. Nine days after the inoculation, the untreated checks were uniformly infected while the treated plants showed the following results:

| | % Disease Control at Indicated Dosage, ppm | | | |
|---|---|---|---|---|
| Treatment | 1200 | 300 | 75 | 19 |
| TC? ?-H | 95 | 95 | 90 | 40 |
| EDPD | 93 | 90 | 25 | 0 |

EXAMPLE 8

Rice plants inoculated with rice blast (*Pyricularia oryzae*), were treated with a 1200, 300, 75 and 19 ppm dilution series of TCPT-H two days after the inoculation. EDPD was used as a comparison. Following treatment the rice plants were moved to conditions conducive to the development of infection. After nine days, the untreated checks showed uniform infection of rice blast while the treated plants showed the following curative activity:

| | % Disease Eradication at Indicated Dosage, ppm | | | |
|---|---|---|---|---|
| Treatment | 1200 | 300 | 75 | 19 |
| TCPT-H | 95* | 90* | 25 | 0 |
| EDPD | 100 | 100 | 90 | 0 |

*Slight phytotoxicity

EXAMPLE 9

Tobacco Black Shank Plant Protectant

A 10,000 ppm concentrate of TCPT-H was prepared in acetone and four fourfold dilutions were then prepared, also in acetone. One ml of each dilution was then added to 100 ml water giving a 100, 25, 6.2, 1.5 ppm dilution series. A similar dilution series was prepared for a comparison compound, 2-chloro-6-methoxy-4-(trichloromethyl)pyridine (pyroxychlor). Small tobacco seedlings were then transplanted into 2-inch pots of soil infested with tobacco black shank (*Phytophthora parasitica var nicotianae*). Immediately after transplanting the pots were drenched with the test and comparison solutions—two pots per dilution and 40 ml of solution per pot. The pots were then placed into the greenhouse for the remainder of the experiment and were watered daily. Seven days after treatment, the untreated checks were dead and the test was graded with the following results:

| | % Control at Indicted Dosage, ppm | | | |
|---|---|---|---|---|
| Treatment | 100 | 25 | 6.2 | 1.5 |
| TCPT-H | 100* | 100* | 100* | 100 |
| Pyroxychlor | 100* | 100 | 100 | 100 |

*Slight phytotoxicity

EXAMPLES 10–18

Various Fungal Plant Protectant Uses

For the following tests, 50% wettable powders were formulated of TCPT-H and of comparison compounds, tricyclohexyl hydroxy stannane (TCHT-H) and triphenyl hydroxy stannane (TPT-H), and a dilution series of 100, 25, 6.2 and 1.5 ppm in 20% isopropanol in water was prepared from each. The dispersions were applied to the host plants the day before inoculation. The tests were graded at the time that the untreated checks became uniformly infected.

*Plasmopara viticola* (Grape Downy Mildew)

| | % Disease Control at Indicated Dosage, ppm | | | | |
|---|---|---|---|---|---|
| Treatment | 100 | 25 | 6.2 | 1.5 | .4 |
| TPT-H | 95 | 90 | 50 | 25 | 0 |
| TCHT-H | 85 | 50 | 0 | 0 | 0 |
| TCPT-H | 99 | 99 | 75 | 0 | 0 |

*Podosphaera leucotricha* (Apple Powdery Mildew)

| | % Disease Control at Indicated Dosage, ppm | | | | |
|---|---|---|---|---|---|
| Treatment | 100 | 25 | 6.2 | 1.5 | .4 |
| TPT-H | 0 | 0 | 0 | 0 | 0 |
| TCHT-H | 93 | 50 | 0 | 0 | 0 |
| TCPT-H | 100 | 100 | 97 | 67 | 25 |

*Erysiphe cichoracearum* (Cucumber Powdery Mildew)

| | % Disease Control at Indicated Dosage, ppm | | | | |
|---|---|---|---|---|---|
| Treatment | 100 | 25 | 6.2 | 1.5 | .4 |
| TPT-H | 0 | 0 | 0 | 0 | 0 |
| TCHT-H | 10 | 0 | 0 | 0 | 0 |
| TCPT-H | 100* | 95 | 50 | 15 | 0 |

*Uromyces phaseoli* (Bean Rust)

| | % Disease Conrol at Indicated Dosage, ppm | | | | |
|---|---|---|---|---|---|
| Treatment | 100 | 25 | 6.2 | 1.5 | .4 |
| TPT-H | 95 | 90 | 75 | 0 | 0 |
| TCHT-H | 67 | 0 | 0 | 0 | 0 |
| TCPT-H | 93 | 85 | 50 | 0 | 0 |

*Venturia inaequalis* (Apple Scab)

| | % Disease Control at Indicated Dosage, ppm | | | | |
|---|---|---|---|---|---|
| Treatment | 100 | 25 | 6.2 | 1.5 | .4 |
| TPT-H | 99 | 90 | 75 | 75 | 0 |
| TCHT-H | 85 | 25 | 0 | 0 | 0 |
| TCPT-H | 99 | 85 | 40 | 0 | 0 |

*Pyricularia oryzae* (Rice Blast)

| | % Disease Control at Indicated Dosage, ppm | | | | |
|---|---|---|---|---|---|
| Treatment | 100 | 25 | 6.2 | 1.5 | .4 |
| TPT-H | 75 | 50 | 40 | 0 | 0 |
| TCHT-H | 50 | 15 | 0 | 0 | 0 |
| TCPT-H | 100 | 99 | 25 | 0 | 0 |

*Puccinia recondita* (Wheat Leaf Rust)

| | % Disease Control at Indicated Dosage, ppm | | | | |
|---|---|---|---|---|---|
| Treatment | 100 | 25 | 6.2 | 1.5 | .4 |
| TPT-H | 75 | 50 | 25 | 0 | 0 |
| TCHT-H | 0 | 0 | 0 | 0 | 0 |
| TCPT-H | 75 | 25 | 0 | 0 | 0 |

*Erysiphe polygoni* (Bean Mildew)

| | % Disease Control of Indicated Dosage, ppm | | | | |
|---|---|---|---|---|---|
| Treatment | 100 | 25 | 6.2 | 1.5 | .4 |
| TPT-H | 0 | 0 | 0 | 0 | 0 |
| TCHT-H | 0 | 0 | 0 | 0 | 0 |
| TCPT-H | 75 | 25 | 0 | 0 | 0 |

*Uncinula necator* (Grape Powdery Mildew)

| | % Disease Control of Indicated Dosage, ppm | | | | |
|---|---|---|---|---|---|
| Treatment | 100 | 25 | 6.2 | 1.5 | .4 |
| TPT-H | 100 | 100 | 85 | 0 | 0 |
| TCHT-H | 100 | 100 | 15 | 0 | 0 |
| TCPT-H | 100* | 100 | 40 | 0 | 0 |

*Slight phytotoxicity

EXAMPLES 19-25

A series of analogs of tricyclopentyl hydroxy stannane, i.e., tricyclopentyl stannane with other counter-ions, were formulated as 50% wettable powders. The compounds were tested as foliar sprays for protectant activity against grape downy mildew, rice blast, wheat leaf rust and apple mildew; and for curative activity against apple scab. All were tested at 400 ppm concentrations prepared by dispersing the required amounts of formulation in 20% isopropanol in water.

The compounds were also tested as soil drenches for control of tobacco black shank at 25 ppm and Verticillium wilt of cotton (*V. albo-atrum*) at 100 ppm. In both of these cases, the chemicals were prepared by dispersing the required amounts of formulation in water. The plants were grown in 2-inch pots and 40 ml of drench was applied per pot.

The chemicals were also tested for control of two-spotted spider mites as foliar treatments and root drench systemics, each test being run at 500 ppm. The test results obtained are as follows:

| Test Compound | Grape Downy Mildew | Apple Scab | Rice Blast | Tobacco Black Shank | Wheat Leaf Rust | Vert. Wilt | Apple Mildew | Spider Mite Protec. | Spider Mite System |
|---|---|---|---|---|---|---|---|---|---|
| 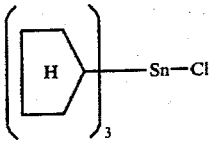 | 100 | 99 | 90 | 100 | 75 | 0 | 100 | 100 | 80 |
| 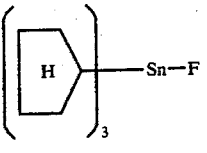 | 100 | 0 | 90 | 0 | 0 | 0 | 100 | 100 | 100 |
| 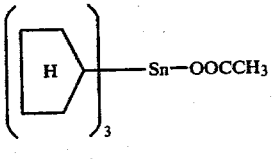 | 100 | 67 | 90 | 0 | 75 | 0 | 100 | 99 | 90 |
| 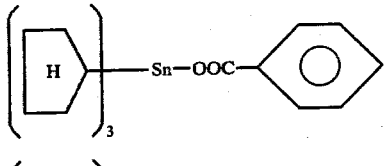 | 100 | 100 | 0 | 100 | 83 | 0 | 100 | 99 | 0 |
| 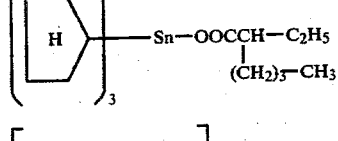 | 100 | 100 | 0 | 100 | 83 | 0 | 100 | 100 | 0 |
| 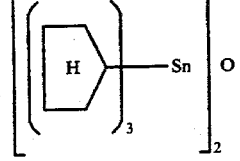 | 100 | 95 | 90 | 0 | 75 | 100 | 100 | 80 | 0 |
| 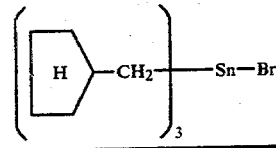 | 97 | 0 | 100 | 100 | 0 | 0 | 90 | 100 | 80 |

EXAMPLES 26-31

A series of tricyclopentyl or tricyclopentyl methyl stannanes with various counter-ions were formulated as 50% wettable powders. The compounds were tested as 400 ppm foliar sprays for protectant activity against grape downy mildew, rice blast, wheat leaf rust and apple mildew; and for curative activity against apple scab. In the rice blast, wheat leaf rust and apple mildew tests, the compounds were simultaneously tested as root drench systemics at 100 ppm. The compounds were also tested as soil drenches for control of tobacco black shank and tobacco black root rot (*Thielaviopsis basicola*), both at 25 ppm, and Verticillium wilt of cotton at 100 ppm. The dilutions were prepared in the same manner as discussed in Example 1. The chemicals were also tested for control of two-spotted spider mites as foliar treatments and root drench systemics, each test being run at 500 ppm. The test results obtained were as follows:

cup with water and an additional application (approx. 20 lbs/acre) of the same test compound is applied to the root area of each plant with a hand syringe. The test is conducted under green house conditions and the percent control is recorded after making correction for natural mortality in untreated checks. Five days after treatment with TCPT-H, the treated plant showed the following control:

| Test Compound | % Control in Indicated Test | | | | | | | | Spider Mite | |
|---|---|---|---|---|---|---|---|---|---|---|
| | Grape Downy Mildew | Apple Scab | Rice Blast | Tobacco Black Shank | Wheat Leaf Rust | Vert. Wilt | Apple Mildew | Tobacco Black Root Rot | Protec. | Systemic |
| [(H⟩—CH$_2$)$_3$—Sn—Cl] | 90 | 0 | 70 | 0 | 90 | 0 | 100 | 0 | 100 | 0 |
| [(H⟩)$_3$—Sn—SC(=S)N(CH$_3$)$_2$] | 100 | 0 | 90 | 100 | 100 | 0 | 100 | 0 | 97 | 0 |
| [((H⟩—CH$_2$)$_3$—Sn)$_2$O] | 100 | 92 | 60 | 100 | 90 | 0 | 99 | 0 | 98 | 17 |
| [(H⟩)$_3$—Sn—S—P(=S)(OC$_2$H$_5$)$_3$] | 100 | 93 | 95 | 100 | 90 | 0 | 100 | 100 | 98 | 0 |
| [(H⟩)$_3$—Sn—SCN] | 100 | 100 | 0 | 100 | 50 | 0 | 90 | 0 | 100 | 0 |
| [((H⟩)$_3$—Sn)$_2$S] | 100 | 95 | 0 | 100 | 0 | 0 | 0 | 100 | 100 | 0 |

EXAMPLE 32

Plant Insecticide Combining Contact Poison, Stomach Poison and Systemic Soil Application

Before the primary leaves of bean plants growing in three-inch plastic pots of vermiculite are fully expanded, fifty to one hundred mites (two-spotted spider mite: *Tetranychus urticae*) are placed on each of the host plants confined in a small plastic cup. The infested plants are then dipped into an aqueous dispersion of the test compound (500 ppm concentration) and each plant pot is then placed into a shallow 4 inch diameter plastic

| Treatment | % Miticidal Control at 500 ppm |
|---|---|
| TCPT-H | 100 |
| Untreated checks | 0 |

EXAMPLE 33

Since control of the screening concentration in Example 32 above may be due to either the plant and insect dip, or the soil treatment or to the combination of both, a test of the active materials against a series of the same concentrations using dip and soil injection separately is conducted.

(a) Contact plus Stomach Poison

Fifty to one hundred mites were placed on their bean host plants and leaves and each infested plant dipped in an aqueous dispersion of the test compound. Treated plants infested with mites were held from 3 to 6 days for insect mortality checks and the treated plants showed the following results:

| Treatment | % Miticidal Control at Indicated Dosage, ppm | | |
|---|---|---|---|
| | 400 | 100 | 25 |
| TCPT-H | 100 | 100 | 0 |
| Untreated checks | 0 | 0 | 0 |

(b) Systemic Soil Application

Bean plants were grown singly in three-inch pots vermiculite and 50 to 100 mites were placed on the primary leaves, infesting each plant before soil injection. Then each plant was placed into a plastic cup where the injection of the test solution onto the soil (vermiculite) at the base of the plant was made with a hand syringe with a long needle. The roots of the infested plants were submerged in this aqueous solution for about 3–6 days after treatment and the treated plants showed the following results:

| Treatment | % Miticidal Control at Indicated Dosage, ppm | | |
|---|---|---|---|
| | 400 | 100 | 25 |
| TCPT-H | 100 | 100 | 100 |
| Untreated checks | 0 | 0 | 0 |

(c) The contact plus stomach poison (infested plant dipped) test method as described in (b) above is tested again, this time against comparison compounds Benomyl (a strong fungicide and very weak miticide) and TCHT-H (a strong miticide and a weak fungicide). In this test four rates of each chemical were evaluated in replicate tests, $R_1$ and $R_2$.

| Treatment | % Miticidal Control | | |
|---|---|---|---|
| | Dosage ppm | $R_1$* | $R_2$* |
| TCPT-H | 100 | 98 | 100 |
| | 25 | 94 | 98 |
| | 6.2 | 94 | 98 |
| | 1.5 | 85 | 60 |
| Benomyl | 100 | 90 | 50 |
| | 25 | 0 | 0 |
| | 6.2 | 0 | 0 |
| | 1.5 | 0 | 0 |
| TCHT-H | 100 | 98 | 100 |
| | 25 | 99 | 100 |
| | 6.2 | 97 | 99 |
| | 1.5 | 85 | 99 |
| Untreated checks | — | 0 | 0 |

*4-day reading based on adults and nymphs only

EXAMPLE 34

On repeating the procedure of Example 5 with apple seedlings which are infested with about 100 2-spotted spider mites each as well as inoculated with apple powdery mildew substantially the same excellent control of the fungal organisms is observed in seedlings treated with TCPT-H of 100 ppm and 25 ppm concentration, respectively, and the mites are also controlled, while substantially no effect is observed on the mite population of the seedlings treated with benomyl dispersion.

EXAMPLE 35

On repeating the procedures of Examples 11 and 13 with apple seedlings and bean seedlings respectively each infested with about 100 two-spotted spider mites as well as the fungal organisms described in the said preceding examples substantially the same fine control of apple powdery mildew is observed in the apple seedlings treated with at least 6.2 ppm TCPT-H while the mites are also well controlled. In the case of the bean plants bean rust is controlled in plants treated with at least 25 ppm TCPT-H and the mites are also well controlled. In those plants treated with TCHT-H only partial control of bean rust is observed at 100 ppm while the mites are well controlled. In those plants treated with TPT-H bean rust is controlled at 25 ppm or greater but there is substantially no effect on the mite populations.

EXAMPLES 36–47

On repeating parts of Examples 19–31 in which each of the apple seedlings are not only inoculated with apple powdery mildew but infested with two-spotted spider mites before treatment with the triorganotin compounds there set forth, similar excellent control of the fungal organisms and of the mite populations is observed in the same plants as set forth for the separate tests.

EXAMPLES 48–53

On repeating parts of Examples 22, 23, 26, 27, 28 and 29 in which each of the wheat seedlings are not only inoculated with wheat leaf rust but also infested with about 100 two-spotted spider mites before treatment with the triorganotin compounds there set forth substantially the same fine control of wheat leaf rust is observed while the mite population is also controlled.

We claim:

1. A method of protecting plants from each of plant pathogenic fungal organisms and mites in the same treatment which comprises:

applying to the said plants to be protected an amount of at least one compound of the formula:

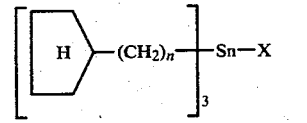

or

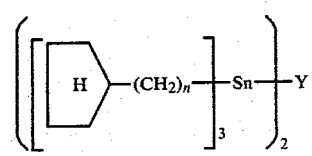

wherein

X is selected from the group consisting of hydroxyl, bromo, chloro, fluoro,

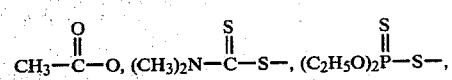

-continued

n is 0 or 1; and
Y is a chalcogen selected from O or S;
which amount is at least an effective antifungal amount and likewise at least an effective miticidal amount, but less than a substantially phytotoxic amount.

2. The method of claim 1 wherein n is 1.

3. The method of claim 2 wherein the compound is selected from tris(cyclopentylmethyl) chlorostannane, tris(cyclopentylmethyl) bromostannane and hexacyclopentylmethyl distannoxane.

4. The method of claim 1 wherein the compound is hexacyclopentyl distannoxane.

5. The method of claim 1 wherein n is 0 and X is hydroxy, chloro,

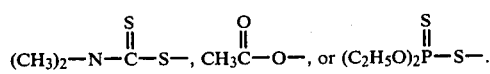

6. The method of claim 5 wherein X is hydroxy.

7. The method of claim 1 wherein the said compound is applied as an aqueous dispersion in a concentration in the range of about 25 to about 600 ppm by weight.

8. The method as in claim 7 wherein the concentration of the said compound is about 100 to about 300 ppm.

9. The method as in claim 7 wherein the compound has the formula

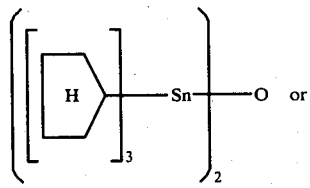

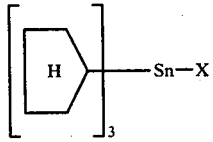

wherein X is hydroxy, chloro,

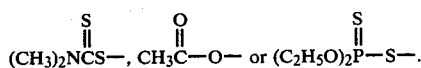

10. The method as in claim 9 wherein X is hydroxy.

11. The method as in claim 8 wherein the compound is tricyclopentyl hydroxystannane.

12. The method as in claim 8 wherein the compound is hexacyclopentyl distannoxane.

13. The method of claim 1 wherein n is 0 and X is fluoro.

14. The method of claim 7 wherein n is 0 and X is fluoro.

15. A composition which consists essentially of an inert or liquid carrier and from about 0.0025 to about 95 percent by weight of a compound of the formula:

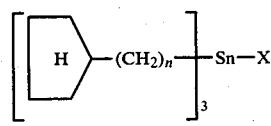

or

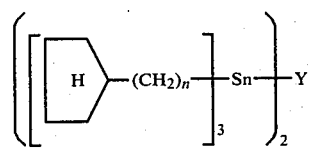

wherein:
X is hydroxyl, bromo, chloro, fluoro,

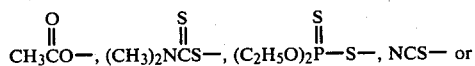

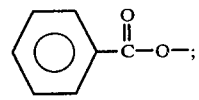

n is 0 or 1; and
Y is oxygen or sulfur;
or a mixture consisting of such compounds.

16. The composition as in claim 15 containing from about 5 to about 95 percent by weight of the said compound or said mixture thereof.

17. The composition as in claim 15 containing from about 20 to about 90 percent by weight of the said compound or said mixture thereof.

18. The composition as in claim 15 containing a miticidally and fungicidally effective amount of said compound or said mixture thereof in the range of about 25 to about 600 ppm.

19. The composition as in claim 15 containing a miticidally and fungicidally effective amount of said compound or said mixture thereof in the range of about 100 to about 300 ppm.

20. The composition as in claim 16 wherein n in the formula is 0.

21. The composition as in claim 20 wherein X is fluoro.

22. The composition as in claim 18 wherein n in the formula is 0.

23. The composition as in claim 20 wherein X is fluoro.

24. The composition as in claim 15 wherein the carrier is an inert solid.

25. The composition as in claim 24 wherein n in the formula is 0.

26. The composition as in claim 25 wherein X is fluoro.

27. The composition as in claim 15 wherein the carrier is an inert liquid.

28. The composition as in claim 27 in the form of an emulsion concentrate containing a water immiscible solvent and an emulsifying agent.

29. The composition as in claim 28 in which n in the formula is 0.

30. The composition as in claim 29 containing from about 5 to about 95 percent by weight of said compound or said mixture thereof.

31. The composition as in claim 30 wherein X is fluoro.

32. The composition as in claim 27 in which, in the formula, n is 0, X is fluoro and the said compound or mixture of compounds is present in a concentration in the range of about 25 to about 600 parts per million.

33. A composition for killing fungi, mites and insects, the composition consisting essentially of an inert liquid or solid carrier and an insecticidally effective amount of tricyclopentyltin fluoride.

34. A composition for killing fungi, mites and insects on living plants, the composition consisting of an inert liquid or solid carrier and a miticidally or insecticidally effective amount of a triorganotin hydroxide of the formula

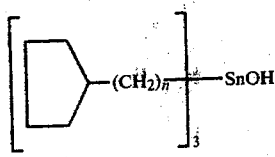

or a bis triorganotin oxide of the formula

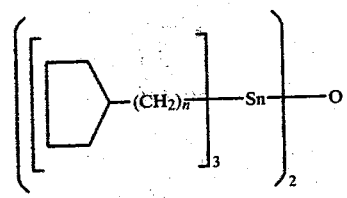

wherein n represents the integer 0 or 1.

* * * * *

UNITED STATES PATENT AND TRADEMARK OFFICE
CERTIFICATE OF CORRECTION

PATENT NO. : 4,224,338

DATED : September 23, 1980

INVENTOR(S) : Ronald J. Sbragia et al

It is certified that error appears in the above-identified patent and that said Letters Patent are hereby corrected as shown below:

Col. 2, line 54, "pytotoxic" should read -- phytotoxic --.

Col. 6, line 7, "for" should read -- four --.

Col. 7, line 10, the word TCPT-H is not legible.

Col. 7, line 54, "Indicted" should read -- Indicated --.

Col. 8, line 27, "Conrol" should read -- Control --.

Col. 15, line 9, "or" should read -- and --.

Col. 15, line 10, should read, which said amount is at least an effective antifungal.

Signed and Sealed this

Twenty-ninth Day of September 1981

[SEAL]

Attest:

GERALD J. MOSSINGHOFF

Attesting Officer

Commissioner of Patents and Trademarks